US012582761B2

(12) United States Patent
Leroy et al.

(10) Patent No.: US 12,582,761 B2
(45) Date of Patent: Mar. 24, 2026

(54) SURGICAL DEVICE COMPRISING A ROD HAVING A DEFORMABLE SLEEVE AT ITS DISTAL END SURROUNDING SAID ROD

(71) Applicants: INSTITUT HOSPITALO-UNIVERSITAIRE DE CHIRURGIE MINI-INVASIVE GUIDEE PAR L'IMAGE, Strasbourg (FR); INSTITUT DE RECHERCHE CONTRE LES CANCERS DE L'APPAREIL DIGESTIF IRCAD, Strasbourg (FR)

(72) Inventors: Joël Leroy, Bouvigny-Boyeffles (FR); Amilcar Alzaga, Mexico City (MX)

(73) Assignees: INSTITUT HOSPITALO-UNIVERSITAIRE DE CHIRURGIE MINI-INVASIVE GUIDEE PAR L'IMAGE, Strasbourg (FR); INSTITUT DE RECHERCHE CONTRE LES CANCERS DE L'APPAREIL DIGESTIF IRCAD, Strasbourg (FR)

( * ) Notice: Subject to any disclaimer, the term of this patent is extended or adjusted under 35 U.S.C. 154(b) by 1018 days.

(21) Appl. No.: 17/638,982

(22) PCT Filed: Aug. 31, 2020

(86) PCT No.: PCT/FR2020/051517
§ 371 (c)(1),
(2) Date: Feb. 28, 2022

(87) PCT Pub. No.: WO2021/038177
PCT Pub. Date: Mar. 4, 2021

(65) Prior Publication Data
US 2022/0296803 A1 Sep. 22, 2022

(30) Foreign Application Priority Data

Aug. 30, 2019 (FR) .................................. FR1909554

(51) Int. Cl.
| | |
|---|---|
| *A61M 1/00* | (2006.01) |
| *A61B 17/22* | (2006.01) |
| (Continued) | |

(52) U.S. Cl.
CPC ................ *A61M 1/84* (2021.05); *A61M 1/79* (2021.05); *A61M 1/87* (2021.05);
(Continued)

(58) Field of Classification Search
CPC .......... A61B 17/221; A61B 2017/0225; A61B 2017/2215
(Continued)

(56) References Cited

U.S. PATENT DOCUMENTS

| | | | |
|---|---|---|---|
| 4,324,262 A * | 4/1982 | Hall | ................... A61M 25/0119 606/127 |
| 5,171,223 A | 12/1992 | Herzberg | |
| (Continued) | | | |

FOREIGN PATENT DOCUMENTS

| | | |
|---|---|---|
| WO | WO-1980001353 A1 | 7/1980 |
| WO | WO-2012009675 A2 | 1/2012 |

OTHER PUBLICATIONS

International Search Report and Written Opinion of the International Search Authority, issued in PCT/FR2020/051517, mailed Oct. 30, 2020; ISA/EP.
(Continued)

*Primary Examiner* — Emily L Schmidt
*Assistant Examiner* — Martin A Radomski
(74) *Attorney, Agent, or Firm* — Harness, Dickey & Pierce, P.L.C.

(57) ABSTRACT

The disclosure relates to a surgical device comprising a rod having a deformable sleeve at its distal end surrounding the
(Continued)

rod, the control element being longitudinally movable for moving the proximal end of the sleeve between a rest position, in which the deformable sleeve has a tubular shape, and an active position, in which the sleeve is deformed by bringing together its distal and proximal ends. The rod is made up of an internal hollow tubular element surrounded by a sheath that can move in translation and rotation relative to the internal hollow tubular element. The distal end of the sleeve is fixed onto a peripheral strip of the internal hollow tubular element and the proximal end of the sleeve is fixed onto a peripheral strip of the sheath.

18 Claims, 5 Drawing Sheets

(51)  Int. Cl.
      *A61B 17/221*           (2006.01)
      *A61B 17/32*            (2006.01)
(52)  U.S. Cl.
      CPC ... *A61B 2017/22079* (2013.01); *A61B 17/221* (2013.01); *A61B 2017/2215* (2013.01); *A61B 17/32* (2013.01)
(58)  Field of Classification Search
      USPC .......................................................... 604/27
      See application file for complete search history.

(56)                    References Cited

U.S. PATENT DOCUMENTS

| | | | | |
|---|---|---|---|---|
| 6,361,545 | B1 * | 3/2002 | Macoviak | A61B 17/221 606/151 |
| 6,626,861 | B1 * | 9/2003 | Hart | A61M 25/10 604/96.01 |
| 2002/0042628 | A1 * | 4/2002 | Chin | A61B 17/12022 606/200 |
| 2003/0176884 | A1 * | 9/2003 | Berrada | A61F 2/0105 606/200 |
| 2005/0187570 | A1 * | 8/2005 | Nguyen | A61B 17/32056 606/159 |
| 2007/0093692 | A1 | 4/2007 | Leroy et al. | |
| 2007/0179458 | A1 | 8/2007 | Leroy et al. | |
| 2008/0269557 | A1 | 10/2008 | Marescaux et al. | |
| 2008/0269562 | A1 | 10/2008 | Marescaux et al. | |
| 2009/0054733 | A1 | 2/2009 | Marescaux et al. | |
| 2011/0152823 | A1 * | 6/2011 | Mohiuddin | A61B 17/221 604/500 |
| 2013/0123800 | A1 | 5/2013 | Leroy et al. | |
| 2013/0345519 | A1 * | 12/2013 | Piskun | A61B 17/0057 600/204 |
| 2014/0005712 | A1 | 1/2014 | Martin | |
| 2014/0046130 | A1 | 2/2014 | Marescaux et al. | |
| 2015/0272716 | A1 * | 10/2015 | Pinchuk | A61F 2/0108 606/200 |
| 2015/0366650 | A1 * | 12/2015 | Zi | A61F 2/0105 606/200 |
| 2018/0000482 | A1 | 1/2018 | Alzaga et al. | |
| 2018/0028181 | A1 | 2/2018 | Alzaga et al. | |
| 2018/0070968 | A1 * | 3/2018 | Wallace | A61B 17/3205 |
| 2018/0206865 | A1 | 7/2018 | Martin et al. | |
| 2018/0325535 | A1 * | 11/2018 | Skillrud | A61B 17/0218 |
| 2019/0159784 | A1 | 5/2019 | Sananes et al. | |
| 2020/0036910 | A1 | 1/2020 | Alzaga et al. | |
| 2020/0234449 | A1 | 7/2020 | Regensburger et al. | |
| 2020/0250835 | A1 | 8/2020 | Alzaga et al. | |
| 2021/0068821 | A1 | 3/2021 | Alzaga et al. | |
| 2021/0073993 | A1 | 3/2021 | Regensburger et al. | |
| 2021/0085398 | A1 | 3/2021 | Alzaga et al. | |
| 2021/0128154 | A1 | 5/2021 | Alzaga et al. | |
| 2022/0015733 | A1 | 1/2022 | Regensburger et al. | |
| 2022/0022964 | A1 | 1/2022 | Alzaga | |

OTHER PUBLICATIONS

French Office Action in French Patent Application No. 20 775 699.0 dated Mar. 11, 2023.
INPI French Search Report, issued in FR 1909554, mailed Apr. 21, 2020.

* cited by examiner

[Fig. 1]
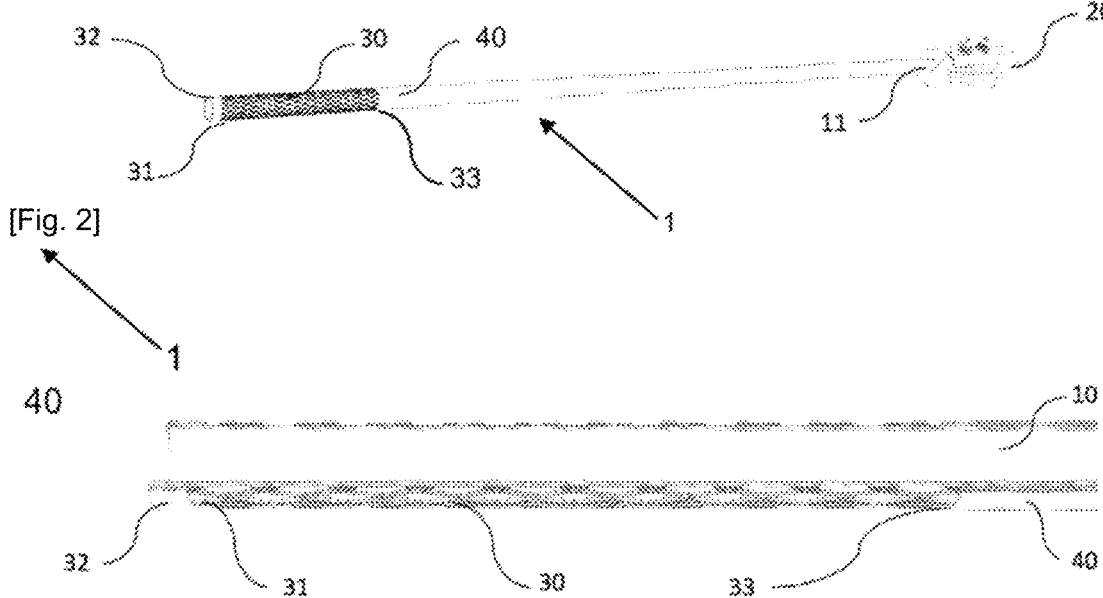
[Fig. 2]
[Fig. 3]
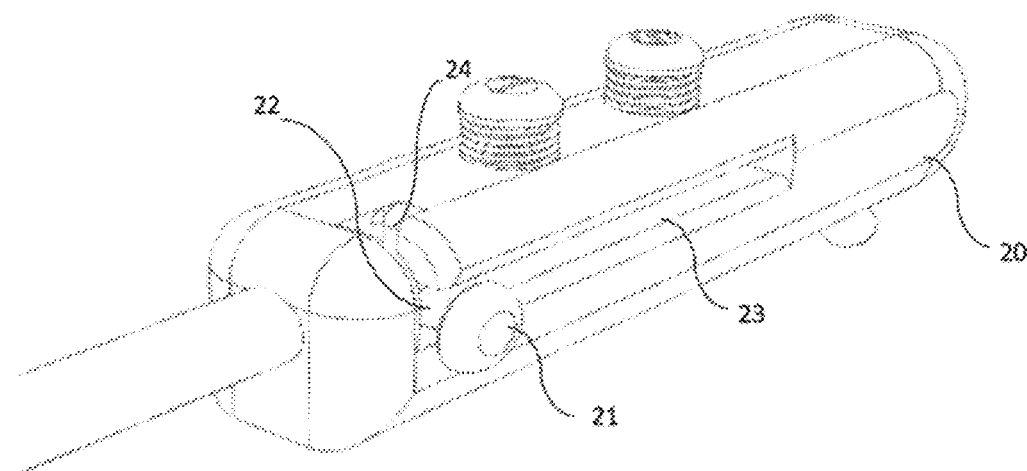

[Fig. 4]
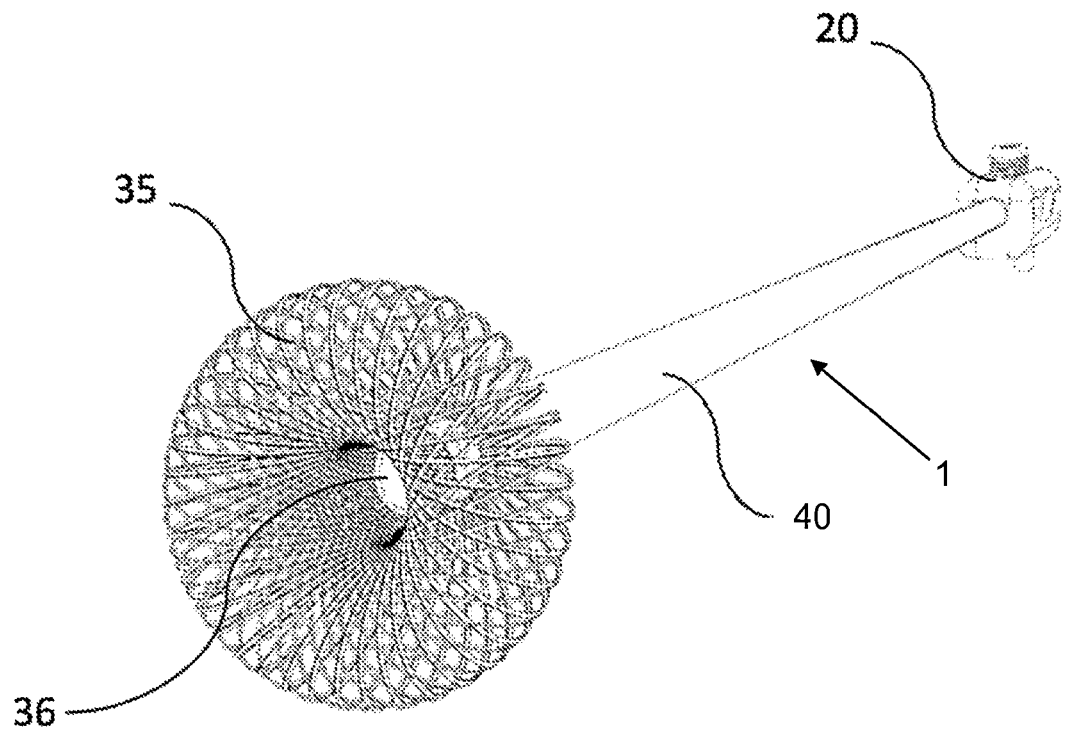

[Fig. 5]
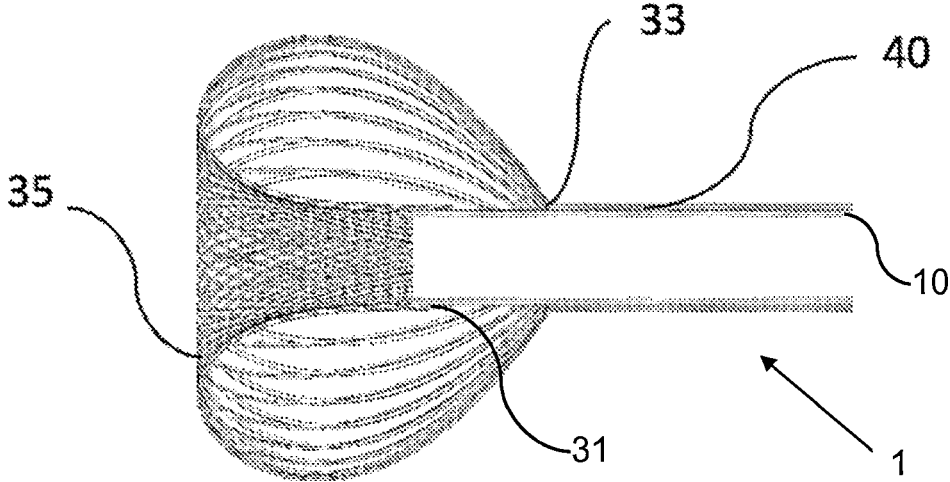

[Fig. 6]
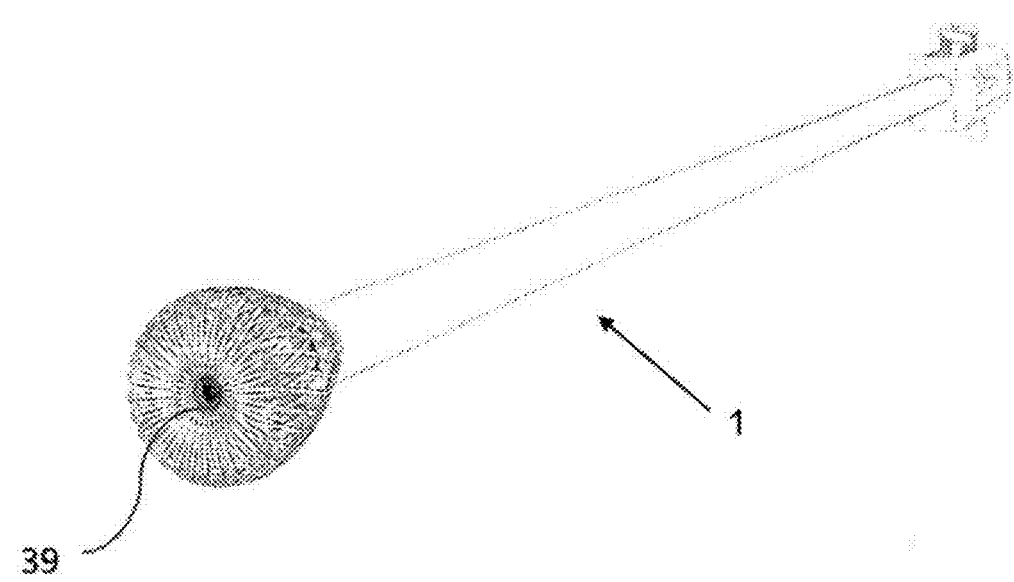

[Fig. 7]
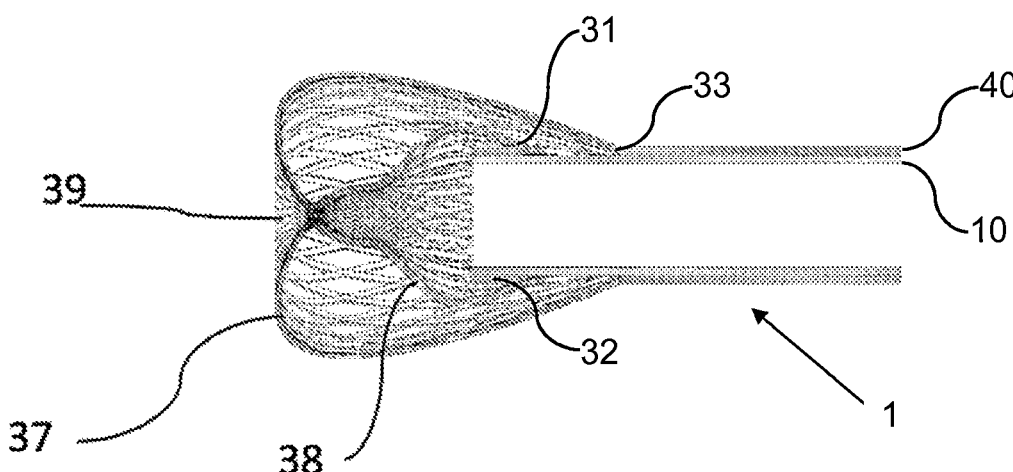

SURGICAL DEVICE COMPRISING A ROD HAVING A DEFORMABLE SLEEVE AT ITS DISTAL END SURROUNDING SAID ROD

CROSS-REFERENCE TO RELATED APPLICATIONS

This application claims priority to PCT Patent Application Serial No. PCT/FR2020/051517 filed on Aug. 31, 2020, which claims priority to the French Patent Application Serial No. FR1909554 filed Aug. 30, 2019, both of which are incorporated by reference herein.

TECHNICAL FIELD

The present invention generally relates to medical devices and more particularly to the field of surgical devices intended to be used in minimally invasive or open surgical procedures to manipulate medical instruments in cavities of a living body, in particular in the field of celioscopy or laparoscopy, such as hooks for implanting suture threads, forceps of any kind, for example for cutting, removing, etc. an organ or a portion of an organ, electrodes, for example to incise, cut, suture, coagulate, to aspirate fluids and semi-solid debris, to aspirate fluids in the presence of bulky debris without clogging, to irrigate the operation area, to dissect and retract tissues without damaging them. Such surgical devices generally consist of a guide tube comprising a through hole of substantially cylindrical shape of revolution opening out respectively at its proximal and distal ends, a cylindrical control rod generally of revolution with an outer diameter smaller than the diameter of the hole and slidably mounted in the guide tube, and means for attaching a medical instrument of any kind, these attachment means being mounted in cooperation with the distal end of the control rod. The outer diameter of the control rod is determined such that it is smaller than the diameter of the through hole so that there is an annular space between the control rod and the wall of the through hole, such that it is possible to blow in a gas under a certain pressure in order to expand the wall of the cavity in which the instrument must be used, and therefore to facilitate the work of the practitioner by increasing the space around the point on which he must intervene medically.

The tube may be of the rigid type, for celioscopic and laparoscopic applications, or flexible, for endoscopic applications. An endoscope comprises a rigid elongated rod or a flexible cord surrounded by a waterproof sheath. The rigid rod or the flexible cord is passed through in a sealed manner in the longitudinal direction by a working channel that is open at the distal end and that opens at the proximal end in the body of a handle. The working channel is used for the passage of working instruments over the entire length of the endoscope to the intervention area. The sheath that surrounds the working channel in an impermeable manner contains, in its internal volume, the devices necessary for the use of the endoscope, in particular an optical instrument, a lighting device, in the form for example of a bundle of conventional optical fibers, or other devices such as electronic devices or instruments for endotherapy or microsurgery. The working channel is also used for the circulation of a fluid. For this purpose, a side outlet conduit is provided, to which extension flow pipes may be connected.

As a rule, the proximal end of the working channel may be closed on the side of the handle by a valve and the outlet conduit may be opened by another valve, so that a cleaning liquid, for example, may be injected through the distal part of the working channel to the intervention area or aspirated from it. The discharge pipe may also, for example, be used for suction or gas admission.

BACKGROUND

Known in particular in the state of the art is a solution described by patent application US2014/005712 describing different variants of devices for use throughout the body, in particular to rid the vascular system of obstructions, by a funnel-shaped head made of a mesh material to hold debris in the vascular system, e.g. blood clot, plaque, cholesterol, thrombus, naturally occurring foreign bodies (i.e. a part of the body that is lodged within the lumen), a non-naturally occurring foreign body, such as a portion of a medical device or other non-naturally occurring substance lodged within the lumen. The funnel device described in this prior patent comprises a flexible rod, a funnel having a distal opening and a proximal portion connected to the rod and a cavity therebetween such that when the funnel is extended, the funnel tapers in a proximal direction toward the rod. The mesh funnel is flexible and the mesh inner wall and mesh outer wall are slidable relative to one another such that removing the device causes movement of the mesh inner wall while a portion of the mesh outer wall remains fixed when positioned against the wall. The deformation of this funnel is ensured by a translational movement of the flexible rod.

U.S. Pat. No. 4,324,262 is also known concerning an embodiment of a probe suitable for introduction into a body cavity, such as a bronchial tube or the lung, for the purpose of biopsy, introducing a fluid and/or sampling a fluid. After the probe is introduced into a bronchial tube, the inner tube is elongated to open and pass through the fold, thereby rolling the inner wall about the folded portion and reversing the inner walls of the pristine chamber.

U.S. Pat. No. 5,171,223 discloses a luxation-proof drainage and instrument duct for arthroscopy comprising a hollow cylinder and a sleeve that are longitudinally displaceable thereupon and which are interconnected at one end, while the sleeve, in the area of its connection end, is constructed in such a way that when the sleeve is moved toward the connection plane, a terminal area of the sleeve is expanded outward in a basket-like manner over the circumference of the sleeve, the basket-like expanded sleeve end being provided with a plurality of perforations arranged so as to be distributed over the circumference and in side-by-side arrangement. The sleeve is stopped on the hollow cylinder in the expanded state of the terminal section of the sleeve.

The solutions of the prior art are not entirely satisfactory. The solution described in patent US2014/005712 proposes a sleeve deployable by a longitudinal guide, to form a collection bag to recover the elements that could obstruct the cannula. Pre-recovery of debris prevents the cannula from clogging, but an additional step must be taken during surgery: evacuation of the waste collected in the collection bag. This may lead to an extension of the intervention time. The operation of the prior art solutions does not allow debris to be apprehended effectively, since the translational movement may lead to the debris being pushed back into the vascular conduit and may possibly lead it into a bifurcation toward a secondary conduit where it will be more difficult to apprehend.

SUMMARY

In order to address these drawbacks, the invention relates, in its most general sense, to a surgical device. Advantageously, said control element is formed by a tube surrounding said rod or said flexible cord. According to a first variant, said deformable sleeve is formed by a porous film.

According to a second variant, said deformable sleeve consists of a wire mesh. According to a third variant, said deformable sleeve consists of a mesh of steel wires. According to a fourth variant, said deformable sleeve consists of a mesh of stainless steel wires with a cross-section of between 150 and 300 micrometers.

Preferably, said deformable sleeve forms a filter having lumens with a section of less than 2 millimeters. Advantageously, the device comprises a handle comprising a control button movable along a linear stroke, to move the proximal end of the sleeve between a rest position and a folded position, and an angular stroke when said control button has reached said folded position.

BRIEF DESCRIPTION OF DRAWINGS

The present invention will be better understood on reading the following description, relative to a non-limiting embodiment of the invention illustrated by the appended figures, in which:

FIG. 1 shows a perspective view of a device according to the invention;

FIG. 2 shows a partial cutaway view of the guide of the device according to the invention;

FIG. 3 shows a perspective view of the handle of the device according to the invention;

FIG. 4 shows a ¾ front perspective view of the distal end in the open position;

FIG. 5 shows a sectional view along a longitudinal plane of the distal end in the open position;

FIG. 6 shows a ¾ front perspective view of the distal end in the closed position; and FIG. 7 shows a sectional view along a longitudinal plane of the distal end in the closed position.

DETAILED DESCRIPTION

Device Hardware Description

By convention, in the present patent, the parts furthest from the handle will be referred to as "distal" and those which are closest to the operator will be referred to as "proximal." In a known manner, the surgical device comprises a tubular rod (1), the proximal end (11) of which is engaged in a handle (20) comprising the control valves for the suction and injection conduits, the connections with additional equipment and the control buttons. The tubular rod (1) according to the invention consists of a hollow inner tubular element (10) surrounded by a sheath (40) sliding around the hollow tubular element (10) with two degrees of freedom, namely:

freedom of relative rotational movement of the hollow inner tubular element (10) with respect to the sheath (40), and freedom of relative translational movement of the hollow inner tubular element (10) with respect to the sheath (40).

The tubular rod (1) formed by the hollow inner tubular element (10) and the sheath (40) moreover has a flexibility allowing deformation of the tubular rod (1) in order to follow the anatomical conformation of the vessel to be treated. The distal end of the rod (1) is surrounded by a tubular deformable sleeve (30), surrounding the distal segment of the tubular element (10). This sleeve (30) is preferably formed by a mesh assembly of wires and extends between the distal end of the tubular element (10) and the distal end of the sheath (40). These two ends of the sleeve (30) are fixed respectively on the end of the tubular element (10) and the end of the sheath (40) in order to allow exertion of a deformation by retraction, by a relative displacement in translation of the hollow inner tubular element (10) with respect to the sheath (40), and in torsion, by a relative displacement in rotation of the hollow inner tubular element (10) with respect to the sheath (40).

This relative displacement is controlled by a handle (20) comprising means for actuating the proximal ends of the hollow inner tubular element (10) relative to the sheath (40), in translation and in rotation. The handle (20) also has:

a suction channel connected to a suction device an irrigation channel connected to an irrigation device The two channels join into one at the proximal end of the two concentric tubes so that suction and irrigation take place through the same orifice at the distal end of the cannula;

A button to actuate the suction

A button to actuate the irrigation

A button to actuate the deployment of the anti-obstruction device, which may be any type of button such as a push button, a wheel, a sliding button, a trigger, etc.

The rod (10) is attached at its proximal end to the handle (20) and allows the administration of irrigation fluids and the removal of bodily fluids and debris.

The distal annular edge (31) of the sleeve (30) is secured to the distal end of the tubular element (10) by a sealing ring (32) that links the distal end (31) of the sleeve (30) with the distal end of the tubular element (10) both in longitudinal translation and in rotation. The proximal end (33) of the sleeve (30) is secured to the sheath (40). The proximal end (33) of the sleeve (30) is secured, in translation and in rotation, with a sheath (40) having a rigidity allowing it to deform as much as the tubular element and sufficient to transmit a longitudinal displacement and/or axial rotation force, exerted at the handle, to the sleeve (30).

This sheath (40) is coaxial with the inner tubular element (10). It is for example made up of a sheath made with a metal profile, for example aluminum. It extends from the proximal end (33) of the sleeve (30) to the handle (20). This handle comprises a mechanism for actuating the sleeve (30) formed by a control button (21) extending a transmission lever (22) sliding in a grid having a first longitudinal segment (23), opening at its distal end onto an arcuate segment (24). The user can move the button (21) with his finger by first sliding the lever (22) in the distal direction, then, when the lever comes into abutment against the bottom of the longitudinal segment (23), rotating axially in the groove (22) to exert a torque on the sheath (40).

Description of the Sleeve

Within the meaning of this patent, the term "sleeve" will be understood to mean an element having a cylindrical shape at rest, generated by parallel generatrixes. At rest and before deformation, the deformable sleeve (30) has a substantially constant cross-section, open at these two ends with a circular cross-section of these openings, that is to say, a surface in space consisting of parallel straight lines. The sleeve (30) is formed by an interlacing of wires arranged helically, according to two series of wires crossing at a constant angle to form regular meshes in a tubular casing of constant cross-section.

At rest, the sleeve (30) forms a tubular element whose internal section corresponds, except for play, to the external section of the tubular element (10). The sleeve (30) is formed by a mesh of metal wires, for example stainless steel wires with a cross-section of between 150 and 300 micrometers forming meshes with lumens having a cross-section of 2 millimeters or less.

Functional Description

When the user pushes the sheath (40) in the distal direction, the latter pushes back the rear (proximal) end of the sleeve (30), which will be subjected to a stress deforming it by "shrinking" it on itself, then by causing an expansion in the form of a torus (35) when the proximal end (33) of the sleeve approaches its distal end (31). FIGS. 4 and 5 illustrate this situation, which occurs when the sleeve exerts a purely longitudinal force, without rotation. The torus (35) that forms is open with a central well (36), and allows flows and debris to pass through the conduit without any blockage.

When an angular force is caused on the sheath (40), the sleeve (30) twists, which causes the formation of a double torus (37, 38) with a closed intersection (39) forming a constriction closing the rod (1) inlet vein. FIGS. 6 and 7 illustrate this situation. This device allows easy switching from an open cannula to a closed cannula by the sleeve (30) owing to the deployment button (21) that is present on the handle (20) and allows the surgeon to avoid having to take the aspirator out of the patient if he wants to go from an open cannula to a closed one.

The filter sleeve (30) may therefore be in three different states:

Retracted=around and along the tubular element (10) for insertion through a trocar Deployed by translation, leaving the distal end port open to suction small debris (open deployed position)

Deployed by translation/rotation, which allows closure of the distal end orifice to prevent obstruction of the device (closed deployed position). In this position, the sleeve has a rigidity allowing the user to place it in contact with the tissues on which he wishes to suck liquid without the sleeve collapsing on itself.

An aspirator-irrigator according to the invention may have other uses described below, such as retracting organs and tissues as well as blunt dissection of tissues or anatomical structures. In order to allow blunt dissection, it is essential for the distal end of the device to have sufficient rigidity in order to exert sufficient force on the tissues when the instrument presses against the tissues in order to dissect them. Such stiffening of the end of the device may in particular be achieved by applying a translation in the proximal direction to the proximal end (33) of the sleeve (30) after the latter has been placed in the deployed position by translation/rotation.

This translation in the proximal direction of the proximal end (33) of the sleeve (30) may be applied by applying a translation in the proximal direction to the sheath (40) secured to the proximal end (33) of the sleeve (30). This translation in the proximal direction of the proximal end (33) of the sleeve (30), once the latter is in a state deployed by translation/rotation, has the effect of "packing down" the sleeve, thus increasing its rigidity and reaching a new state.

In one version of the invention, the control member is adapted to allow the translation in the proximal direction after the translation in the distal direction and the rotation of the sleeve. In a sub-variant where the control is manual and carried out by an operator's hand, this translation in the proximal direction of the sleeve is carried out by means of a handle adapted to gripping, for example comprising a slide. In a sub-variant where the control is manual and carried out by an operator's hand, this translation in the proximal direction of the sleeve is carried out by means of a handle adapted to gripping, for example comprising a slide, the handle further comprising a spring. This spring may for example be compressed by the user when the latter moves a slide in order to carry out the first translation, the energy of the spring being released, after the rotation, in order to carry out the second translation in the proximal direction this time.

Using the Device

The device according to the invention allows a modification of the input configuration of the rod to be controlled from the handle so as to allow all the flows to pass through the suction conduit, or to selectively filter the components based on their size and/or their viscosity. The device according to the invention allows easy switching between the filtration mode where the distal end is permeable only to liquids and the suction mode for blood clots, debris or solids.

The filter sleeve (30) in the retracted position is of a thickness such that it allows effortless and risk-free entry into the incision sizes conventionally present during minimally invasive surgical procedures. Once in the body cavity, the filter sleeve (30) is able to be deployed easily and quickly by action of a dedicated button present on the handle. When deployed, the filter sleeve (30) partially or completely covers the suction hole, thus preventing debris and solids from interfering with the passage of fluids. The porous nature of the filter allows for unhindered suction of bodily fluids.

A major drawback of the known devices resides in the fact that the organs and soft tissues (the small intestine, the adipose tissues, the mesentery, the omentum) or large clots may easily be sucked into the lumen of the cannula. In minimally invasive surgery, the surgeon must then stop the suction and use another tool to unclog the aspirator, and if this is not possible, the aspirator must then be taken out to clean it outside the patient. It may be necessary to unclog the suction device several times during one single surgical operation, with the following consequences:

disrupted workflow for the surgeon and other staff, and extended duration of procedures and therefore increased i. risks for the patient ii. fatigue of the surgical team iii. and total cost of the operation.

Untimely interruption of suction is a major problem with available aspirator-irrigators.

Most of the existing solutions having a device that allows prevention of clogging in the cannula do not allow the suction of semi-solid debris. It also allows the addition of new functionalities, namely suction of fluids and/or semi-solid debris, filtration of solid debris, tissue dissection and organ retraction in complete safety. The deployable filter sleeve (30) allows solid debris to be filtered and blunt dissection to be performed safely, while retaining the ability to suction fluids and semi-solid debris when the filter is in the retracted position.

Surgeons have become accustomed to using suction-irrigation devices for purposes other than suction and irrigation, and in particular to dissect tissues and move organs. Known suction devices are generally made up of a metal cannula that is not protected at the distal end. There is therefore a possibility of causing tissue damage during the use of these devices in uses that are not originally intended.

Retraction consists in displacing organs or moving them away from the operative field of vision. In digestive surgery for example, for many operations it is necessary to remove the liver and keep it thus removed for the duration of the operation in order to access and then operate on the organs located below. The aim being to maintain the organ out of the field of vision, the operation of maintaining the organ in this separated position is not carried out under visual oversight. It is crucial that the instrument used be atraumatic so as not to damage the retracted organs. Devices dedicated to tissue retraction that are compatible with endoscopic and in particular laparoscopic approaches have been developed, such as fan retractors. However, their use requires the removal of another surgical instrument in order to allow the insertion of these devices that are dedicated exclusively to tissue retraction. The device according to the invention advantageously allows performance of suction or irrigation, then retraction or displacement of tissues or organs without an instrument exchange being necessary.

Collateral uses include gentle tissue retraction: while the filter sleeve (30) is deployed, it is rigid enough to allow for gentle tissue dissection and retraction.

To displace tissues and organs in complete safety owing to the anti-obstruction device, which extends beyond the distal end of the inner tubular member (10)

To prevent contact between the tip of the cannula and the tissues during suction owing to the deployment of the anti-obstruction device beyond the distal end of the inner tubular element (10).

During surgery, several dissection methods are used. One of them is foam dissection: this is done without cutting or using energy (electricity, ultrasound). In open surgery, it is performed with the finger: the surgeon separates the tissues by applying pressure and imparting translational movements. It is a very safe and very commonly used dissection.

In endoscopic and particularly laparoscopic surgery, the surgeon cannot insert his hands into the operation area. An instrument is therefore necessary to perform this dissection. Instruments dedicated to blunt dissection and specific to laparoscopy have, for example, been developed. These consist of a long handle, at the end of which a bulb is fixed composed of gauze or dense wadding.

Another collateral use of the invention is the blunt dissection of tissues and anatomical structures: while the filter sleeve (30) is deployed, it is rigid enough to allow the blunt dissection of tissues. Devices dedicated exclusively to blunt dissection that are compatible with endoscopic and in particular laparoscopic approaches have thus been developed; however, their use requires the removal of another surgical instrument in order to allow the insertion of these devices dedicated exclusively to blunt dissection. The device according to the invention advantageously allows performance of suction or irrigation, then blunt dissection without an exchange of instruments being necessary.

For example, during a laparoscopic cholecystectomy, the invention may be used as an irrigating aspirator during the dissection in order to clean the operation area, to suck up the water used for irrigation, to suck up the blood and potentially bile that may spill out during the procedure. This step may be carried out without risk of occlusion if the sleeve is in the deployed position.

In addition, the invention may be used to retract the liver in order to expose the vesicle without risk of damaging the surface thereof. Finally, the invention may be used for dissection: for example, to separate the vesicle from the surface of the liver without incision or use of an energy source. Advantageously, this dissection may be done in a controlled and safe manner because, after deployment by translation, then rotation, the sleeve is homogeneous and atraumatic but sufficiently dense to allow blunt dissection.

In certain variants of the invention, the user will have the possibility of subjecting the sleeve to a translation in the proximal direction after deployment by rotation in order to pack it down and therefore to increase the hardness of the bulb formed by the sleeve. It is thus possible to adapt the rigidity of the end of the device both to the user's preferences and to the tissues encountered.

Use in Robotics

An aspirator-irrigator according to the invention will be of interest in robotic use, where the exchange of instruments is more complex and time-consuming than in a conventional approach. For example, in robotic laparoscopy, an additional incision is sometimes made on the patient's abdomen in order to introduce a non-robotic aspirator-irrigator. In a variant of the invention, the control member is a robotic interface adapted to be mounted on a robot arm or the arm of a remote manipulator.

The control member could for example integrate several interfaces allowing robotic actuation of the instrument. These may comprise interfaces allowing the movement of the various mobile elements of the invention: translation or rotation of the sheath or even interfaces allowing the actuation of suction or irrigation.

The device according to the invention is particularly suitable for robotic surgical procedures, using an endoscopic robot. The introduction and progression of the rod, then the actuation in translation, then in torsion are ensured by actuators controlled by a computer allowing automation of the recovery of a clot or of a body to be isolated. This sequence of translation of the control element, then of axial rotation, then of additional translation to pack down the body caught in the sleeve may be controlled by the computer, for example when the operator triggers the start of the sequence by a unique instruction.

Surgical Applications

During vascular surgery or other surgical specialties focusing on soft organs (gynecology, urology, digestive surgery, etc.), one of the determining steps is accessing the structure or organ on which the procedure must take place. Several dissection techniques are typically used consecutively to separate, divide or remove tissue. During these dissections, bleeding may occur; in this case it is useful to suck up the blood or other fluids polluting the view of the operation area. Sometimes it is necessary to suck up clots or small solid debris. In order to clean the operation area, it is also useful to use irrigation to remove opaque fluids preventing good visualization of the operation area. If an aspirator according to the invention is used, with the sleeve deployed by translation and rotation, the aspiration may be carried out without risk of untimely obstruction of the end of the cannula. For example, it will not be necessary to use compresses or some other improvised filter in order to prevent occlusion of the end. If a clot or debris is encountered during the procedure, the user can easily place the sleeve in the retracted position in order to suck it out.

When it is necessary during the procedure to retract an organ in order to keep it away from the operation area, the user will place the sleeve in the deployed position by translation and rotation in order to ensure atraumatic contact with the retracted organ. It will then not be necessary to remove the aspirator from the patient to introduce a dedicated retractor. For example, it is necessary to retract the liver during a gastric bypass operation: the liver is held on the left side of the patient in contact with the abdominal wall in order to expose the stomach and the small intestine, which are the target structures for this procedure.

When blunt dissection is necessary in order to separate tissues, the user can place the sleeve in the deployed position by rotation and translation in order to separate the tissues completely atraumatically. Here again, it will therefore not be necessary to remove an instrument in order to introduce a dedicated blunt dissection instrument.

The aspirator-irrigator according to the invention may be used to perform atraumatic dissections. For example, in the case of gallbladder removal, it must be separated from the liver. This operation may be carried out by means of the invention. The artery and the cystic duct leading to the vesicle must be completely separated and isolated from the surrounding tissues in order to identify them with certainty, clamp them and cut them in order to release the vesicle. This dissection step is here again a separation of tissues that may advantageously be carried out by means of the invention when the sleeve is deployed by translation and rotation. If, during these dissections, the user wished to aspirate or irrigate the area or to retract an organ, he would simply need to modify the deployment of the sleeve using the control member.

The invention claimed is:

1. A surgical device comprising: a rod having a first end and a second end, said rod including: a hollow inner tubular element, said hollow inner tubular element including a terminal hollow tubular element end, and a sheath surrounding said hollow tubular element, said sheath including a terminal sheath end and being configured to be movable translationally and rotationally relative to said hollow inner tubular element; a deformable sleeve surrounding said second end of said rod, said deformable sleeve including a proximal end and a distal end, said proximal end being affixed to said terminal sheath end and said distal end being affixed to said terminal hollow tubular element end; a handle positioned at said first end; and a movable control element positioned on said handle configured to move said proximal end of said deformable sleeve between a rest position, in which said deformable sleeve has a tubular shape, and an active position, in which said deformable sleeve is deformed by bringing together said proximal end and said distal end, the active position comprising an active open position where suction flow into the hollow inner tubular element is unconstricted by the deformable sleeve, wherein when a rotational force is exerted on said control element, said deformable sleeve is configured to form a double torus having a twisted closed intersection between a first torus and a second torus in said active position, the twisted closed intersection forming an active closed position of the deformable sleeve, the twisted closed intersection being aligned with a center of the hollow inner tubular element to restrict material from being suctioned into the hollow inner tubular element.

2. The surgical device according to claim 1, wherein said deformable sleeve is configured to filter the material while allowing fluid passage through said hollow inner tubular element.

3. The surgical device according to claim 1, wherein said deformable sleeve is a porous film.

4. The surgical device according to claim 1, wherein said deformable sleeve includes a wire mesh.

5. The surgical device according to claim 1, wherein said deformable sleeve includes a mesh of steel wires.

6. The surgical device according to claim 1, wherein said deformable sleeve is a mesh of stainless steel wires with a cross-section between 150 and 300 micrometers.

7. The surgical device according to claim 1, wherein said deformable sleeve is a filter having lumens with a cross-section of less than 2 millimeters.

8. The surgical device according to claim 1, wherein said control element is a button movable along a linear stroke, to move said proximal end of said deformable sleeve between said rest position and said active position, and an angular stroke when said deformable sleeve has reached said active position.

9. A surgical device comprising: a rod having a first end and a second end, said rod including: a hollow inner tubular element including a terminal hollow tubular element end, and a sheath surrounding said hollow inner tubular element, said sheath including a terminal sheath end and being configured to be movable translationally and rotationally relative to said hollow inner tubular element; a deformable sleeve surrounding said second end of said rod, said deformable sleeve including a proximal end and a distal end, said proximal end being affixed to said terminal sheath end and said distal end being affixed to said terminal hollow tubular element end; a handle positioned at said first end, said handle comprising a grid having a longitudinal segment and an arcuate segment extending from the longitudinal segment, said handle receiving a movable control element configured to move said proximal end of said deformable sleeve between a rest position, in which said deformable sleeve has a tubular shape, and an active position, in which said deformable sleeve is deformed by bringing together said proximal end and said distal end, the active position comprising an active open position where suction flow into the hollow inner tubular element is unconstricted by the deformable sleeve, wherein when a rotational force is exerted on said control element, said deformable sleeve is configured to form a double torus having a twisted closed intersection between a first torus and a second torus in said active position, the twisted closed intersection forming an active closed position of the deformable sleeve, the twisted closed intersection being aligned with a center of the hollow inner tubular element to restrict material from being suctioned into the hollow inner tubular structure.

10. The surgical device according to claim 9, wherein said control element is a control button movable along the longitudinal segment and the arcuate segment to move said proximal end of said deformable sleeve between said rest position and said active position, and an angular stroke when said deformable sleeve has reached said active position.

11. The surgical device according to claim 9, wherein the twisted closed intersection closes an orifice of the hollow inner tube element.

12. The surgical device according to claim 9, wherein said deformable sleeve is a porous film.

13. The surgical device according to claim 9, wherein said deformable sleeve includes a wire mesh.

14. The surgical device according to claim 9, wherein said deformable sleeve is a filter having lumens.

15. A surgical device comprising:
a rod having a first end and a second end, said rod including:
a hollow inner tubular element including a terminal hollow tubular element end defining an orifice, and
a sheath surrounding said hollow inner tubular element, said sheath including a terminal sheath end and being configured to be movable translationally and rotationally relative to said hollow inner tubular element;
a deformable sleeve surrounding said second end of said rod, said deformable sleeve including a proximal end and a distal end, said proximal end being affixed to said terminal sheath end and said distal end being affixed to said terminal hollow tubular element end;
a handle positioned at said first end, said handle comprising a grid having a longitudinal segment and an arcuate segment extending from the longitudinal segment, said handle receiving a movable control element configured to move said proximal end of said deformable sleeve between a rest position, in which said deformable sleeve has a tubular shape, and an active position, in which said deformable sleeve is deformed by bringing together said proximal end and said distal end, the active position comprising an active open position where suction flow into the orifice and the hollow inner tubular element is unconstricted by the deformable sleeve, wherein when a rotational force is exerted on said control element, said deformable sleeve is configured to form a double torus having a closed intersection between a first torus and a second torus that closes the orifice and is axially aligned with the hollow inner tubular element in said active position.

16. The surgical device according to claim 15, wherein said deformable sleeve is a porous film.

17. The surgical device according to claim 15, wherein said deformable sleeve includes a wire mesh.

18. The surgical device according to claim 15, wherein said deformable sleeve is a filter having lumens.

\* \* \* \* \*